United States Patent [19]

Graves

[11] 4,308,880
[45] Jan. 5, 1982

[54] ANIMATED DENTAL FLOSS DISPENSER

[76] Inventor: Rodney J. Graves, 17619 N. 35th Pl., Phoenix, Ariz. 85032

[21] Appl. No.: 186,139

[22] Filed: Sep. 11, 1980

[51] Int. Cl.³ ............................................. A61C 15/00
[52] U.S. Cl. .................................. 132/92 A; 132/91; 40/421; 40/425; 46/135 R
[58] Field of Search .................... 132/92 A, 92 R, 91, 132/90; 242/137.1, 146; D28/64; 40/421, 423, 425; 46/135 R; 225/39

[56] References Cited
U.S. PATENT DOCUMENTS

| 2,295,430 | 9/1942 | Seewald | 40/421 |
| 2,381,530 | 8/1945 | Dembenski | 132/92 A |
| 2,926,487 | 3/1960 | Stone | 40/421 X |
| 3,225,472 | 12/1965 | Guida | 40/421 |
| 3,746,017 | 7/1973 | Casselman | 132/92 A |

Primary Examiner—Gene Mancene
Assistant Examiner—Mickey Yu
Attorney, Agent, or Firm—Warren F. B. Lindsley

[57] ABSTRACT

An animated dental floss dispenser capable of visually simulating the flossing of a person's teeth and the simultaneous dispensing of dental floss.

7 Claims, 12 Drawing Figures

ANIMATED DENTAL FLOSS DISPENSER

BACKGROUND OF THE INVENTION

It is an established fact that the periodic use of dental floss for disorganizing bacterial plaque always present in tiny crevices near the gum line and between the teeth is recommended by dental authorities as a necessary oral hygiene practice.

Many attempts have been made to make a convenient dispenser for dental floss but most have been merely storage and dispensing devices for floss and few, if any, have been animated in such a way as to encourage the flossing process especially for children and young adults.

FIELD OF THE INVENTION

In view of the importance of performing the flossing function at specified periodic intervals of time, and because the average person is inclined to be apathetic or forgetful about the importance of the precise timing of such functions, a need exists for a suitable reminder means which will also stimulate the viewer to action. It is also evident that if the necessary material, such as dental floss, is conveniently at hand when needed, it would greatly assist in the performance of the flossiing function at the proper time.

DESCRIPTION OF THE PRIOR ART

Various types of timing and dispensing devices have been used for this purpose, such as clocks that may be set to emit a sound at the proper time to get the user's attention and separate dispensing means for the material required.

In such usage, considerable difficulty is usually encountered in coordinating the functiion of the separated timing and dispensing devices because they are often kept in different rooms of the user's home and the sound emitted by the time clock may not be audible to the user at all times.

Therefore, a need exists for a dispensing device that calls the user's attention to the fact that the time has arrived for the performance of oral hygiene implemented by the material dispensed by the device.

Although no prior art relating to the device claimed is known, U.S. Pat. No. 3,746,017 is directed to a dental floss holder and applicator having a floss storage and dispensing reel, floss take-up reel and an arcuate arm to hold floss in application position.

SUMMARY OF THE INVENTION

In accordance with the invention claimed, a new and improved animated dental floss dispenser is provided which is capable of visually simulating the flossing of a person's teeth and the simultaneous dispensing of dental floss.

It is, therefore, one object of this invention to provide a new and improved dental floss dispenser.

Another object of this invention is to provide a new and improved animated dental floss dispenser which visually simulates the flossing of a person's teeth while simultaneously dispensing dental floss.

A further object of this invention is to provide a dental floss dispenser which by its appearance stimulates a viewer to floss his or her teeth.

A still further object of this invention is to provide a new and improved dental floss dispenser which utilizes a simulated version of a person's teeth and mouth together with movable hands simulating a flossing action to encourage young and old to floss their teeth.

A still further object of this invention is to provide an easily portable dispenser that can be hand carried wherever needed.

Further objects and advantages of the invention will become apparent as the description is given and the features of novelty which characterize this invention will be pointed out with particularity in the claims annexed to and forming a part of this specification.

BRIEF DESCRIPTION OF THE DRAWINGS

The present invention may be more readily described by reference to the accompanying drawings in which.

DESCRIPTION OF THE PREFERRED EMBODIMENT

Figure 1:
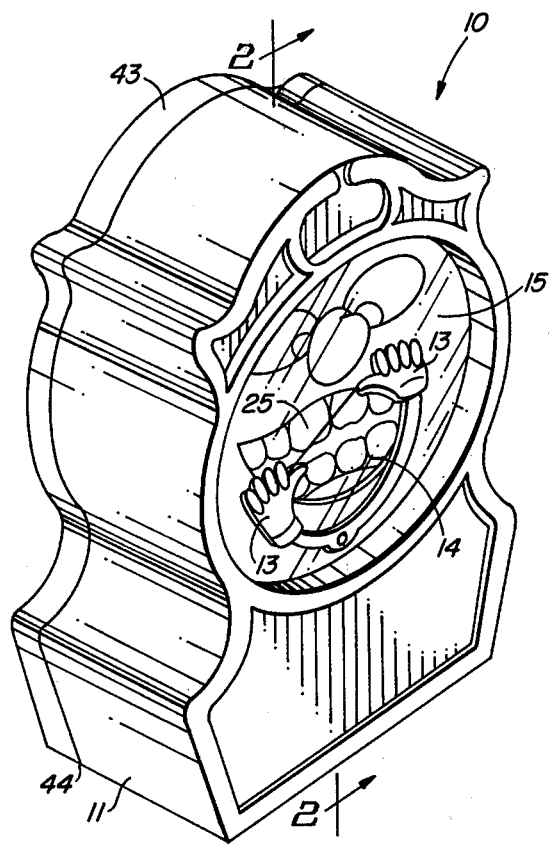
FIG. 1 is a perspective view of an animated dental floss dispenser embodying the invention simulating the flossing of a person's teeth while simultaneously dispensing dental floss.
Figure 2:
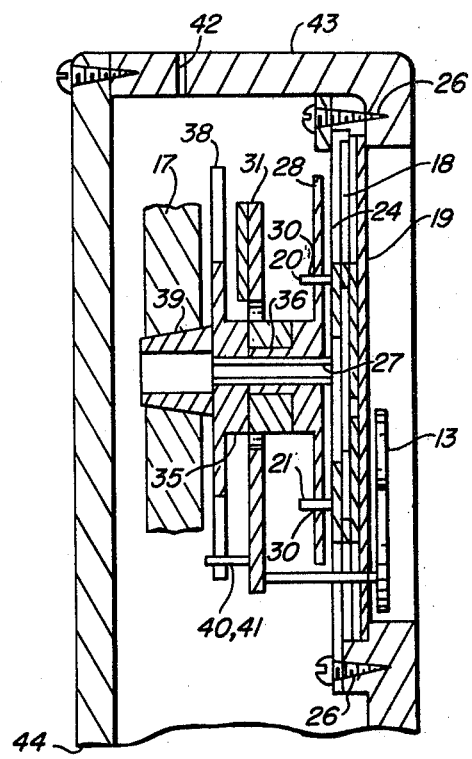
FIG. 2 is a cross-sectional view of FIG. 1 taken along the line 2—2.
Figure 3:
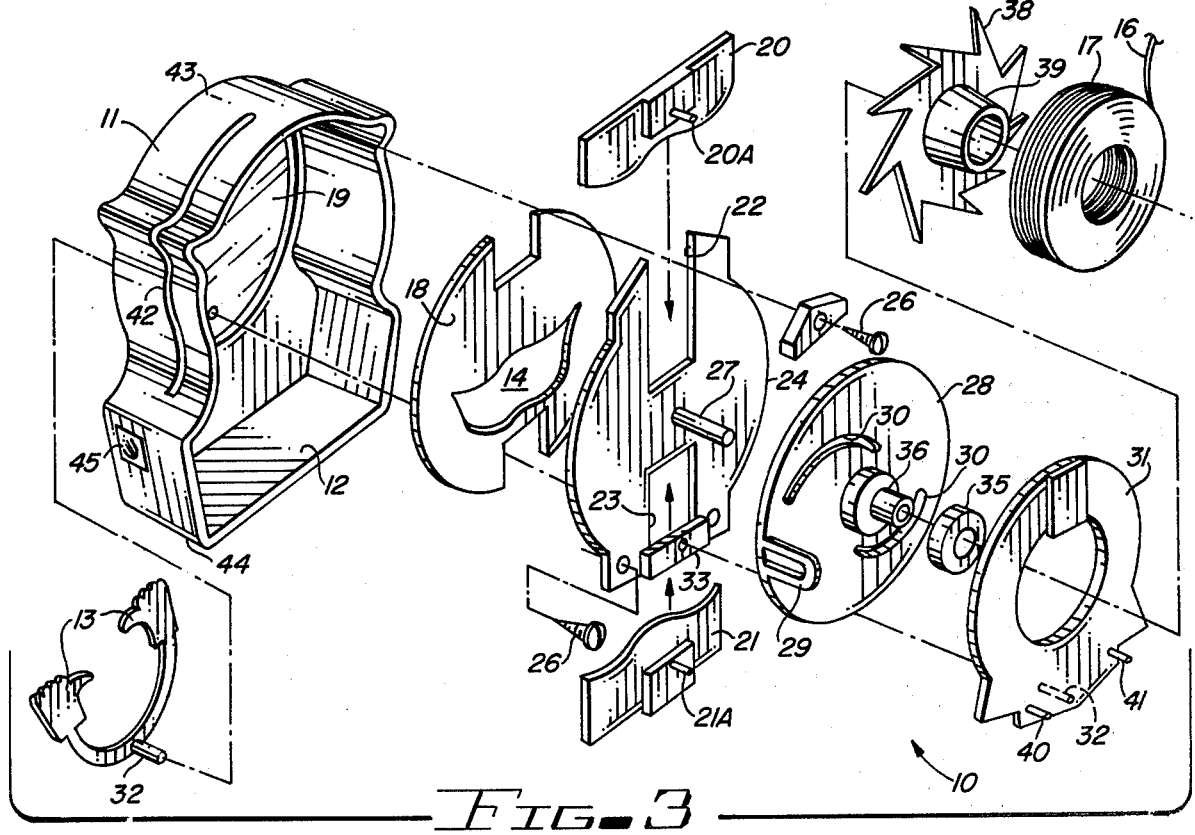
FIG. 3 is an exploded perspective view from the rear of the animated dental floss dispenser shown in FIG. 1.

Referring more particularly to the drawing by characters of reference, FIGS. 1-3 disclose an animated dental floss dispenser 10 having a housing 11 defining a cavity 12 into which the mechanism for moving the hands 13 and mouth 14 of the animated character 15 are mounted.

The purpose of the dispenser is to encourage the removal of dental floss thereby hopefully encouraging its use in a teeth flossing operation. To encourage the removal of dental floss from the dispenser the animated character is provided with a mouth that opens and closes and a pair of hands which move to simulate a flossing operation.

The mechanism for opening and closing the mouth 14 of the animated character 15 as well as moving its hands 13 upon the removal of dental floss 16 from a roll or spool 17 thereof comprises a face plate 18 with mouth opening 14 mounted in an opening 19 in housing 11. A pair of slides 20 and 21 each configured to form a lip display are slidably mounted for reciprocal movement in slots 22 and 23 of a backplate 24. The backplate 24 is provided with teeth display 25 as shown in FIG. 1. The backplate 24 together with face plate 18 are fixedly secured to housing 11 by any suitable means such as, for example, screws 26 shown in FIGS. 2 and 3.

Figure 4A:
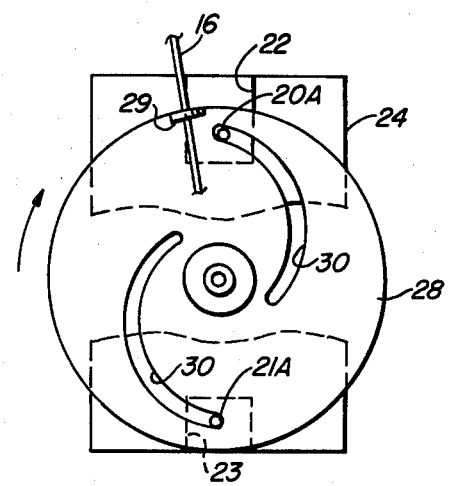
FIGS. 4A and 4B are front views of the cam disk with floss engaging prongs shown in FIGS. 2 and 3, the movement of the floss opening and closing the mouth of the animated character shown in FIG. 1.
Figure 4B:
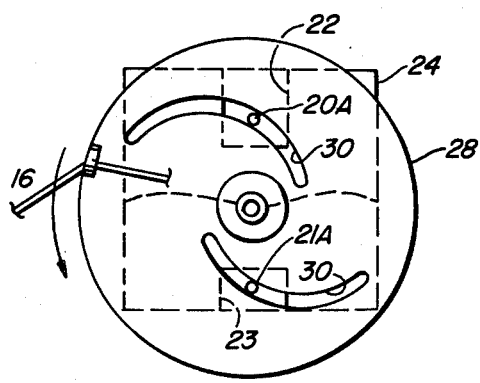
Figure 5A:
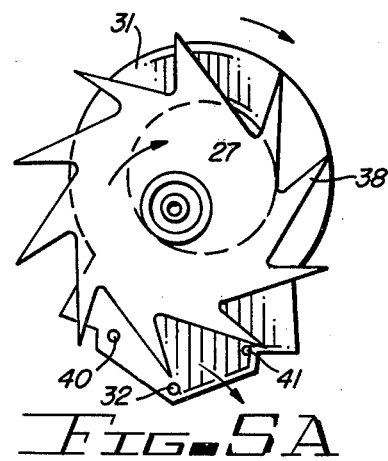
FIGS. 5A and 5B are front views of the escapement disk and floss holding spindle in two different driven positions.
Figure 5B:
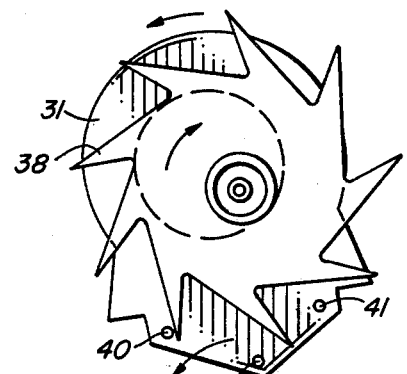

As shown in FIG. 3, the backplate 24 is provided with a rod 27 extending axially therefrom rearwardly of the mechanism for rotatably supporting thereon a cam disk 28 having a floss engaging prongs 29 extending rearward of the mechanism and laterally thereof. A pair of arcuate slots 30 are formed in cam disk 28, as shown in FIGS. 3, 4A and 4B, for receiving therein pins 20A and 21A of slides 20 and 21 for movement thereof upon rotation of the cam disk.

Juxtapositioned to the cam disk 28 is mounted a pendulum 31 which is pivotally rotatable about a pin 32 extending through it, a plate 33 mounted on backplate 24 rotatably supporting the hands 13 in front of the animated character 15. A spacer 35 mounted on the bearing 36 of cam disk 28 keep the pendulum in proper spaced relationship thereto.

Juxtapositioned to the pendulum is mounted a star, escapement or ratchet disk 38 secured to rod 27 and comprising a floss holding spindle 39 on which is mounted the spool of floss 17. As noted from FIGS. 2 and 3 the pendulum 31 is provided with a pair of spaced pins 40 and 41 which extend laterally thereof for engaging between the teeth of the star gear 38.

Figure 8:
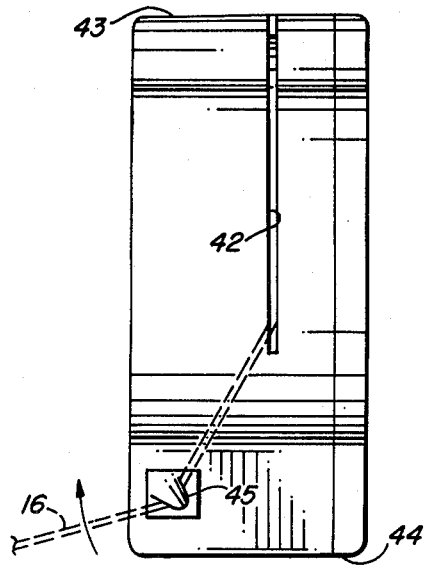
FIG. 8 is a side view of the housing shown in FIG. 3 with a piece of floss in cutting position.

As shown in FIGS. 3 and 8, the housing 11 is provided with a slot 42 extending therethrough in one side thereof extending from the top of the housing 43 toward its bottom 44 through which the floss 16 is withdrawn in a predetermined manner. When the floss is withdrawn a sufficient length and drawn to the bottom of the slot 42, the piece or length of floss withdrawn may be cut off of the roll of floss by the well known cutting edge or blade means 45 mounted near the bottom 44 of the housing.

In operation of the dispenser the user pulls the end of the floss 16 which is fed from spool 17 through prong 29 of cam disk 28 upward through the slot 42 near the top 43 of housing 11. This action causes the prong 29 of cam disk 28 to rotate the cam disk to the position shown in FIG. 4A. The movement of cam disk 28 to the position shown in FIG. 4A causes the pins 20A and 21A of slides 20 and 21 to move slides 20 and 21 away from each other in slots 22 and 23 in backplate 24 exposing the teeth 25 of the animated character 15 and giving the impression of the lips opening.

The movement of the floss 16 off of spool 17 which is tightly mounted on the floss holding spindle 39 causes rotation of the star disk or escapement means 38 against the rocker pins 40 and 41 on the pnedulum 31 which swings back and forth creating the "tick-tock" sound of a clock when its pins 40 and 41 are engaged and also causes the hands 13 to swing from side-to-side giving the effect that the animated character is flossing its teeth.

Figure 6A:
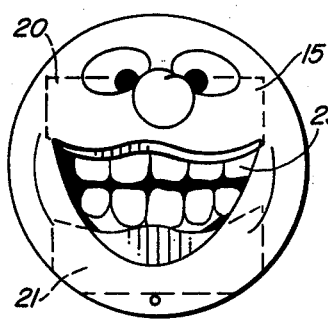
FIGS. 6A and 6B are front views of the animated character in mouth open and mouth closed positions, respectively.
Figure 6B:
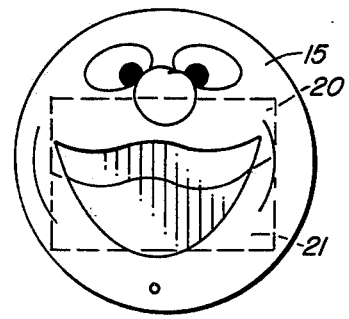
Figure 7A:
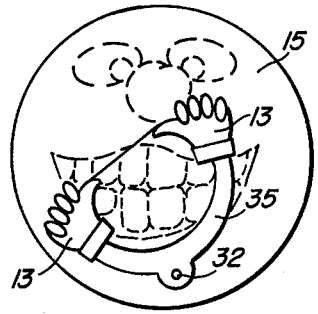
FIGS. 7A and 7B are the views of FIGS. 6A and 6B with hands of the animated character in two different positions.
Figure 7B:
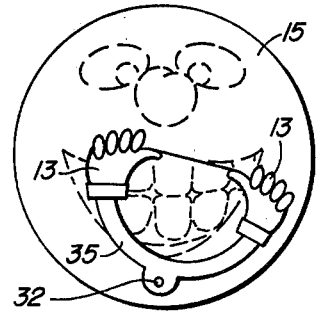

By pulling the floss downwardly in slot 42 toward the base 44 of housing 12 to cut the piece of withdrawn floss off of the spool 17 with cutting blade 45 rotates the cam disk the other direction to the position shown in FIG. 4B. This action causes the slides 20 and 21 to move toward each other closing the lips of the mouth as shown in FIG. 6B and moves the hands 13 to the position shown in FIG. 7B.

It will be apparent to those skilled in the art that changes and other modifications may be made to the apparatus shown and described herein without departing from the spirit of the invention or from the scope of the appended claims.

What is claimed is:

1. An animated dental floss dispenser comprising:
   a hollow housing displaying an animated character through an opening therein;
   said character having a mouth opening,
   a mechanism for animating said character,
   said mechanism comprising a backplate mounted behind said animated character and having a pair of sliding plates mounted thereon for opening and closing said mouth opening,
   said plates having pins extending laterally therefrom,
   a cam disk mounted adjacent said plate for moving said pins and said slide plates in a predetermined direction,
   said cam disk comprising a prong for engaging a piece of floss passing thereover for rotation of said cam disk upon predetermined movement of said floss, and
   a spool of floss mounted adjacent said cam disk,
   said housing having a slot extending therethrough,
   whereby when a piece of the floss from said spool is fed over said prong and through said slot and is pulled toward one end of said slot, said cam disk causes movement of said slide plates relative to each other in one direction and when the piece of floss is pulled toward the other end of said slot, said cam disk causes relative movement of said slide plates in the other direction to open and close said mouth opening of said animated character.

2. The animated dental floss dispenser set forth in claim 1 wherein:
   said animated character is formed in the likeness of a toothie character.

3. The animated dental floss dispenser set forth in claim 2 wherein:
   said slide plates are formed as lips of the animated character.

4. The animated dental floss dispenser set forth in claim 1 in further combination with:
   a pendulum pivotally mounted adjacent said cam disk,
   means for rotatively mountiing a spool of dental floss adjacent said pendulum,
   a spool of dental floss mounted on said means,
   the dental floss when pulled from said spool causing said means to rotate said pendulum back and forth through an arcuate path,
   a pair of hands mounted in front of said mouth opening, and
   means connecting said hands to said pendulum for predetermined movement upon movement of said pendulum.

5. The animated dental floss dispenser set forth in claim 4 wherein:
   said means for rotatively mounting a spool comprises a ratchet gear,
   pin means spacedly mounted on said pendulum for engaging the teeth of said ratchet gear upon rotation thereof.

6. The animated dental floss dispenser set forth in claim 5 in further combination with:
   means for loosely mounting said pendulum on said cam disk so that when said ratchet gear sequentially engages said pin means on said pendulum a tick-tock sound is generated.

7. The animated dental floss dispenser set forth in claim 1 in further combination with:
   a pair of arcuate slots formed in said cam disk with one of said pins of said slide plates extending into each of said arcuate slots,
   whereby rotation of said cam disk causes predetermined movement of said slide plates.

* * * * *